United States Patent
Smiley

(10) Patent No.: US 6,710,018 B2
(45) Date of Patent: Mar. 23, 2004

(54) COMPOSITIONS CONTAINING A DICARBOXYLIC ACID DIESTER AND A POST-EMERGENT HERBICIDE AND A METHOD OF USING THE SAME

(75) Inventor: Robert A. Smiley, Wilmington, DE (US)

(73) Assignee: Falcon Lab LLC, Wilmington, DE (US)

( * ) Notice: Subject to any disclaimer, the term of this patent is extended or adjusted under 35 U.S.C. 154(b) by 17 days.

(21) Appl. No.: 10/443,909

(22) Filed: May 22, 2003

(65) Prior Publication Data

US 2003/0236166 A1 Dec. 25, 2003

Related U.S. Application Data

(60) Provisional application No. 60/389,789, filed on Jun. 19, 2002.

(51) Int. Cl.$^7$ .................. A01N 35/06; A01N 37/10; A01N 47/36; A01N 47/40; A01N 57/04
(52) U.S. Cl. .............. 504/206; 504/211; 504/214; 504/313; 504/323; 504/343; 504/348
(58) Field of Search ................ 504/127, 129, 504/118, 313, 131, 133, 135, 136, 137, 138, 139, 140, 141, 142, 206, 211, 214, 323, 343, 348

(56) References Cited

U.S. PATENT DOCUMENTS

| | | | |
|---|---|---|---|
| 2,603,560 A | 7/1952 | Stewart | 71/2.3 |
| 2,765,224 A | 10/1956 | Lambrech | 71/2.6 |
| 2,852,426 A | 9/1958 | Stanbury | 167/22 |
| 2,942,023 A | 6/1960 | Gordon et al. | 260/468 |
| 2,948,653 A | 8/1960 | Bavley et al. | 167/22 |
| 3,143,408 A | 8/1964 | Smythe et al. | 71/2.5 |
| 3,399,990 A | 9/1968 | Humphrey et al. | 71/11 |
| 3,555,160 A | 1/1971 | Gier et al. | 424/308 |
| 3,652,653 A | 3/1972 | Emerson et al. | 504/313 |
| 3,810,750 A | 5/1974 | Davidson et al. | 71/78 |
| 3,991,100 A | 11/1976 | Hochberg | 260/485 |
| 4,071,348 A | 1/1978 | Abramitis | 71/78 |
| 4,095,973 A | 6/1978 | Maeda et al. | 71/103 |
| 4,123,552 A | 10/1978 | Kensler, Jr. et al. | 424/311 |
| 5,092,918 A | 3/1992 | Kuchikata | 71/94 |
| 6,117,823 A | 9/2000 | Smiley | 504/313 |
| 6,218,336 B1 | 4/2001 | Coleman | 504/118 |
| 6,503,869 B1 | 1/2003 | Beste et al. | 504/127 |

FOREIGN PATENT DOCUMENTS

| | | | |
|---|---|---|---|
| CA | 2099631 | 6/1993 | A01N/25/30 |
| DE | 3321529 A1 | 12/1984 | A01N/37/04 |
| DE | 4319263 A1 | 6/1993 | A01N/25/30 |
| GB | 2309904 A | 8/1997 | A01N/25/00 |
| JP | 42006999 | 3/1967 | |

*Primary Examiner*—S. Mark Clardy
(74) *Attorney, Agent, or Firm*—Locke Liddell & Sapp LLP

(57) ABSTRACT

A method for enhancing the effectiveness of post-emergent herbicides consists of the addition, to the post-emergent herbicidal composition, of an effective amount of a carboxylic acid diester of the formula:

$$ROOC(CH_2)_nCOOR' \qquad (I)$$

wherein R and R' are independently selected from a $C_1$ to $C_4$ alkyl group and n is from about 5 to about 9. The advantages of using a compound of formula (I) with the post-emergent herbicide include a faster visual phytotoxic response, better weed control and use of less post-emergent herbicide.

25 Claims, No Drawings

COMPOSITIONS CONTAINING A DICARBOXYLIC ACID DIESTER AND A POST-EMERGENT HERBICIDE AND A METHOD OF USING THE SAME

This application claims priority to provisional application Ser. No. 60/389,789, filed Jun. 19, 2002.

FIELD OF THE INVENTION

A means of enhancing the effectiveness of post-emergent herbicides comprises the addition of an effective amount of at least one carboxylic acid diester to a post-emergent herbicide.

BACKGROUND OF THE INVENTION

Herbicides are generally classified into two groups—those having significant foliar use and those primarily applied into the soil. Herbicides with significant foliar use, generally described as post-emergent herbicides, are further divided into three major categories based on translocation patterns and initial plant symptoms: (a) translocated herbicides showing initial symptoms on new growth; (b) translocated herbicides showing initial symptoms on older growth; and (c) non-translocated herbicides showing initial localized injury. Each of these categories may further be subdivided according to herbicidal mode of action, i.e., auxin-type growth regulators; aromatic amino acid (EPSDS) inhibitors; branched-chain amino acid (ALS/AHAS) inhibitors; carotenoid pigment inhibitors; lipid biosynthesis (ACCase) inhibitors; organic arsenicals; "classical" photosynthesis inhibitors; "rapidly acting" photosynthesis inhibitors; Photosystem I (PSI) energized cell membrane destroyers; protoporphyrinogen oxidase [Protox (PPO)] inhibitors; and glutamine synthesis inhibitors. Of these, the most popular are glyphosate and salts of glyphosate including the monoammonium, diammonium and isopropyl ammonium salts disclosed in U.S. Pat. Nos. 5,998,332; 4,507,250; 4,481,026; 4,405,531; 4,315,765; 4,140,513; 3,977,860; 3,799,580; and 3,853,530 (including the commercial products Roundup® and Touchdown®), sulfonylurea, (sold under the tradename Classic® by E.I. duPont de Nemours and Co.), glufosinate, first reported as a herbicide in Schwerdtle, et. al. "Z. Pflanzenkr. Pfanzenschutz. Sonderheft IX. p. 431 (and now including the commercial product Finale®), oxyfluorfen, disclosed in U.S. Pat. No. 3,798,276 (and now commercially sold as Goal®), imazamox, discovered by American Cyanamid (now commercially available as Raptor®), clethodim, first reported by Kincade, et. al. in Proc. Br. Crop Prot. Conf. Weeds in 1987 (now commercially sold as Select®), sethoxydim, discovered by Nippon Soda in Japan (now commercially sold as Poast®), quizalofop, disclosed in U.S. Pat. No. 4,629,493 (now commercially sold as Assure®), fenoxaprop, first reported by Bieringer, et. al. in Proc. Br. Crop Prot. Conf. Weeds in 1982 (now commercially sold as Fusion® and Acclaim), fluazifop, disclosed in British Patent 1,599,121 (now commercially sold as Horizon 2000 and Fusilade DX) and bipyridilium salts first disclosed in British Patent 813,531 (commercially sold as Paraquat® and Diquat®) amongst others.

Post-emergent herbicides are generally slow acting and usually take days or even weeks to show a visual effect on the weeds and grasses to which they have been applied. This is undesirable from the user's standpoint. U.S. Pat. No. 5,994,269 discloses a means of achieving a more rapid visual sign of herbicidal activity by the addition of an activator to glyphosate. However, the time to achieve the desired effect is too long. Furthermore, the disclosed method does not permit the use of less post-emergent herbicide. Alternatives are therefore needed.

Along with the need to obtain a faster time for visualization of the herbicidal effect, it is further desired to develop a means which mandates less of the herbicidal active ingredient than is now employed. The reduction in the amount of the herbicidal active ingredient is desired since such chemicals are generally toxic and non-biodegradable.

SUMMARY OF THE INVENTION

It has been discovered that the herbicidal activity of post-emergent herbicides is enhanced by the addition, to the post-emergent herbicide, of least one carboxylic acid diester of the formula:

$$ROOC(CH_2)_nCOOR' \qquad (I)$$

wherein R and R' are independently selected from a $C_1$ to $C_4$ alkyl group and n is from about 5 to about 9. These diesters are based on acids occurring in nature and thus have low toxicity and high biodegradability. Further, the introduction of such diesters to a post-emergent solution, emulsion or suspension permits utilization of reduced amounts of the post-emergent herbicide while still providing effective weed control. Additionally, use of the composition of the invention reduces the time required for systemic phytotoxic symptoms to appear on the target weed.

In accordance with the method of the invention, diesters of $C_7$ to $C_{11}$ linear dibasic acids, usually in admixture with a surfactant or emulsifier, are added to a herbicidal composition and the resulting mixture is applied to the target weed. The target weed starts to wilt and turn brown within hours. Necrosis has been seen, for instance when dimethyl azelate is added to glyphosate, to approach 100% within twenty-four to thirty-six hours of treatment compared to minimal necrosis times of three to four days without the diester.

DETAILED DESCRIPTION OF PREFERRED EMBODIMENTS

The effectiveness of post-emergent herbicides is dramatically improved by addition of a compound of formula (I) to a post-emergent herbicide prior to its application to the vegetation. The compound of formula (I) is at least one carboxylic acid diester of the formula:

$$ROOC(CH_2)_nCOOR' \qquad (I)$$

wherein R and R' are independently selected from a $C_1$ to $C_4$ alkyl group and n is from about 5 to about 9. R and R' on any given compound of formula (I) may be the same or different alkyl group. In a preferred embodiment, n is 7 or 8. Particularly desirable esters are the dimethyl, diethyl, diisopropyl and dibutyl esters. Especially preferred as the carboxylic acid diester of formula (I) are the lower alkyl diesters of pimelic, suberic, azelaic, sebacic and undecanedioic acids, for example, the methyl or ethyl esters. Mixtures of two or more of the carboxylic acid diesters may further be employed.

The composition applied to the vegetation of the invention may further contain a diluent. Any liquid in which formula (I) is soluble or miscible may be employed as a diluent. As a post-emergent, the herbicidal compositions of the invention are preferably applied to the locus of the unwanted vegetation as an aqueous mixture or emulsion.

When a compound of the formula (I) is added to a post-emergent herbicidal composition
  (a) either as a water emulsion or
  (b) by diluting a commercial herbicidal concentrate to a herbicidally effective concentration [with a water emulsion of formula (I)]

and the resulting mixture is applied to weeds according to the herbicide manufacturers recommendation, the weeds exhibit a visual phytotoxic effect in less time than would be obtained with the herbicide in the absence of the compound of formula (I). As an example, weed and grass necrosis may approach 100% within 24 hrs. with glyphosate in combination with dimethyl azelate, compared to 3–4 days or longer without the addition of dimethyl azelate.

Furthermore, with the addition of a compound of formula (I) such as dimethyl azelate, to the post-emergent herbicide, less of the post-emergent herbicide than specified by the manufacturer can be used to achieve the same herbicidal result as would be obtained using the herbicide suppliers' recommended amount in the absence of dimethyl azelate.

The herbicidal composition of the invention containing a compound of formula (I) may be applied to the locus of the unwanted vegetation in effective amounts in the manner normally used with the herbicide without the addition of the compound of formula (I). Concentrations of the post-emergent herbicide in the herbicidal composition of the invention will vary depending on the herbicide and the weeds to be controlled but the concentration of the compound of formula (I) in the final herbicidal composition is preferably between from about 0.5 to about 5.0 % by weight of the herbicidal composition, preferably between from about 1.5% to about 3.0% by weight. This preferred amount of compound of formula (I) is independent of the selection of post-emergent herbicide in the composition. Thus, regardless if the post-emergent herbicide is a sulfonyl urea, which typically is used in amounts approximating 5 to 10 grams per acre, or glyphosate, which typically is used in agricultural sprays in amounts approximating 0.75 to 1.0 weight percent, the amount of compound of formula (I) in the final herbicidal composition is between from about 0.50 to about 5.0 weight percent of the herbicidal composition.

Any post-mergent herbicide, regardless of its mode of action, may be used in combination with the carboxylic acid diester of formula (I). These include those translocated herbicides showing initial symptoms on new growth (Table I); translocated herbicides showing initial symptoms on older growth (Table II); and non-translocated herbicides showing initial localized injury (Table III), as set forth in Ross and Lembi, *Applied Weed Science*, 2d edition, Prentice-Hall, 1999, pp. 156–157:

TABLE I

| TYPE | TRADENAME |
|---|---|
| Auxin-Type Growth Regulators | |
| Phenoxy acid herbicides | |
| 2,4-D | Numerous |
| 2,4-DB | Butoxone, Butyrac |
| 2,4-DP (dichlorprop) | Available only in mixtures |
| MCPA | Rhonox, Rhomene, Sword, Weedon MCPA |
| MCPB | Thistrol |
| MCPP (mecoprop) | MCPP 4K, Mecomec |
| Benzoic acid herbicides | |
| Dicamba | Banvel, Clarity, Vanquish |
| Picolinic acid (pyridinecarboxylic) herbicides and relatives | |
| Clopyralid | Lontrel, Reclaim, Stinger, Transline |
| Picloram | Tordon |
| Triclopyr | Garton, Grandstand, Remedy, Turflon |
| No chemical family recognized | |
| Naptalam | Alanap |

TABLE I-continued

| TYPE | TRADENAME |
|---|---|
| Aromatic Amino Acid (EPSPS) inhibitors | |
| Glyphosate | Accord, Rodeo, Roundup, Roundup Ultra, Touchdown (sulfosate) |
| Branched-Chain Amino Acid (ALS/ARAS) Inhibitors | |
| Sulfonylurea herbicides | |
| Bensulfuron | Londax |
| Chlorimuron | Classic |
| Chlorsulfuron | Glean, Telar |
| Halosulfuron | Manage, Permit |
| Metasulfuron | Ally, Escort |
| Nicosulfuron | Accent |
| Primisulfuron | Beacon |
| Prosulfuron | Peak |
| Rimsulfuron | Matrix |
| Sulfometuron | Onst |
| Thifensulfuron | Pinnacle |
| Triasulfuron | Amber |
| Tribenuron | Express |
| Triflusulfuron | UpBeet |
| Imidazolinone herbicides | |
| Imazamethabenz | Assert |
| Imazamox | Raptor |
| Imazapic | Cadre, Plateau |
| Imazapyr | Arsenal, Chopper, Stalker |
| Imazaquin | Scepter, Image |
| Imazethepyr | Pursuit |
| Triezolopyrimidine sulfonanilide herbicides | |
| Cloransulam | FirstRate |
| Flumetsulam | Broadstrike, Python |
| Pyrimidinyl oxybenzoate herbicides | |
| Pyrithlobac | Staple |
| Carotenoid Pigment inhibitors | |
| No chemical family recognized | |
| Amitrole | Amitrol-T |
| Clomazone | Command |
| Fluridone | Sonar |
| Isoxazole herbicide | |
| Isoxaflutole | Balance |
| Pyridazinone herbicide | |
| Norflurazon | Predict, Solicam, Zorial |
| Lipid Biosynthesis (ACCase) Inhibitors | |
| Aryloxyphenoxy propionate herbicides | |
| Diclofop | Hoelon |
| Fenoxaprop | Acclaim, Whip 1EC |
| Fenoxaprop-P | Acclaim Extra, Option II, Whip 360 |
| Fluazifop-P | Fusilade II, Fusilade DX, Omamic 170 |
| Haloxyfop | Verdict, Gallant |
| Quizalofop-P | Assure II |
| Cyclohexanedione herbicides | |
| Clethodim | Envoy, Prism, Select |
| Sethoxydim | Poast, Poast Plus, Prestige, Torpedo, Ultima, Vantage |
| Tralkoxydim | Achieve |
| Organic Arsenicals | |
| DSMA | Ansar, DSMA Liquid |
| MSMA | Ansar, Arsenate Liquid, Bueno, Daconate |

TABLE I-continued

| TYPE | TRADENAME |
|---|---|
| Unclassified Herbicides | |
| Asulam | Asulox |
| Difenzoquat | Avenge |
| Fosamine | Krenite |
| Propanil | Stam; Stampede |

TABLE II

| "Classical" Photosynthesis Inhibitors | |
|---|---|
| S-Triazine herbicides | |
| Ametryn | Evik |
| Atrazine | Aatrex, Atrazine |
| Cyanazine | Bladex |
| Hexazinone | Velpar |
| Prometon | Pramitol |
| Prometryn | Caparol |
| Simazine | Princep |
| as-Triazine herbicide | |
| Metribuzin | Lexone, Sencor |
| Phenylurea herbicides | |
| Diuron | Kamex |
| Fluometuron | Cotoran |
| Linuron | Lorox |
| Tebuthiuron | Spike |
| Uracil herbicides | |
| Bromacil | Hyvar |
| Terbacil | Sinbar |
| "Rapidly Acting" Photosynthesis Inhibitors | |
| Benzothiadiazole herbicide | |
| Bentazon | Basagran |
| Benzonitrile herbicide | |
| Bromoxynil | Buctril |
| Phenylcarbamate herbicides | |
| Desmedipham | Betanex |
| Phenmedipham | Spin-Aid |
| Pyridazinone herbicide | |
| Pyrazon | Pyramin |
| Phenylpyridazine herbicide | |
| Pyridate | Tough |

TABLE III

| Photosystem I (PS I) Energized Cell Membrane Destroyers | |
|---|---|
| Bipyridilium herbicides | |
| Paraquat | Cyclone, Gramoxone Extra, Starfire |
| Diquat | Diquat, Reward |
| Protoporphyrinogen Oxidase [Protox (PPO)] Inhibitors | |
| Diphenylether herbicides | |
| Acifluorfen | Blazer, Status |
| Fomesafen | Flexstar, Reflex |
| Lactofan | Cobra |
| Oxyfluorfen | Goal |
| Oxadiazole herbicides | |
| Oxadiazon | Ronstar |
| Fluthiacet | Action |

TABLE III-continued

| N-phenylphthalimide herbicide | |
|---|---|
| Flumiclorac | Resource |
| Triazolinone herbicides | |
| Carfentrazone | Affinity, Aim |
| Sulfentrazone | Authority, Cover, Spartan |
| Glutamine Synthesis Inhibitors | |
| Glufosinate | Finale, Liberty, Rely |

Particularly desirable results have been evidenced in herbicidal compositions containing the compound of formula (I) and phenoxy acids, such as 2,4-D; glyphosates (N-phosphonomethylglycines) and ammonium (particularly monoammonium and diammonium) and isopropylammonium salts thereof; glufosinate and salts thereof, sulfonyl urea herbicides, especially rimsulfuron containing herbicides; cyclohexanediones, such as sethoxydim containing herbicides; benzothiadiazole herbicides; diphenylether herbicides especially those containing fomesafen; and bipyridilium herbicides, such as paraquat and diquat.

The method of the invention may be used to control established vegetation in the vicinity of a seeded crop or in a weed concentrate area by contacting the foliage of the unwanted vegetation with the herbicidal composition.

Surfactants, wetting agents, dispersing agents, suspending agents, and/or emulsifying agents may further be employed with the herbicidal composition of the invention. Such materials are typically included in commercial herbicidal formulations, to which may be added the compound of formula (I).

Unwanted vegetation may be killed by applying to the locus of the vegetation the herbicidal composition of the invention. The herbicidal composition of the invention may be contacted with the unwanted vegetation by spraying or otherwise distributing the composition onto the foliage in accordance with the manufacturers' directions of the post-emergent herbicide [to which has been added the carboxylic acid diester of formula (I)]. The herbicides of the invention exhibit several advantages not previously seen with other commercial herbicides. Most importantly, the invention dramatically reduces the kill time. Leaves of vegetation sprayed with herbicidal compositions of the invention usually start to shrivel or turn brown within hours of a single application. Necrosis is evident, usually in 24 hours. Typically unwanted vegetation is dead in less than 24 hours compared to 3 to 4 days when the post-emergent is solely used. Since use of the compound of formula (I) decreases the amount of post-emergent herbicide required, the invention dramatically reduces costs.

Weeds and grasses which may be killed by use of the herbicidal composition of the invention include quack grass, buttercup, common cinquefoil, multi flora rose, common yellow woodsorrel, prostrate spurge, henbit, poison ivy, poison hemlock, common speedwell, broadleaf plantain, Japanese honeysuckle, dandelion, wild violet, Bermuda grass, nutsedge, wild garlic, knotweed, red sorrel, lambs quarters, pokeweed, carpetweed, crabgrass, buckhorn plantain, nimblewill, or common chickweed. Moss, small tree saplings and suckers and shoots from tree roots and tree stumps may also be controlled with the emulsion.

The following examples will illustrate the practice of the present invention in its preferred embodiments. Other embodiments within the scope of the claims herein will be apparent to one skilled in the art from consideration of the specification and practice of the invention as disclosed herein. It is intended that the specification, together with the examples, be considered exemplary only, with the scope and spirit of the invention being indicated by the claims which follow.

EXAMPLE 1

A quart of glyphosate herbicide was prepared using the label recommendations of the manufacturer (Monsanto) by adding 18 ml. (0.625 liq. oz.) of "Roundup® Super Concentrate" (41% isopropyl glyphosate), to water and bringing the final solution to 32 oz. liquid (Sol. A). To another 18 ml. of "Roundup Concentrate" was added 18 ml. of dimethyl azelate and this mixture diluted with water to 32 liq. oz. (Sol. B). Thus, each solution contained the same amount of glyphosate while Sol. B also contained 2% dimethyl azelate.

Sol. A was applied with a hand sprayer on a 2 ft. by 3 ft. plot of ground containing a variety of weeds. Sol. B was applied in the same manner on a similar adjacent plot containing the same variety of weeds. The temperature was in the mid-80's (° F.) during the test period with no rain.

The test plots were observed daily. The results are shown in the following chart:

| WEED | Effect after 1 day | | After 2 days | | After 4 days | | After 14 days | |
|---|---|---|---|---|---|---|---|---|
| | A | B | A | B | A | B | A | B |
| Carpetweed | 0 | 3 | 1 | 3 | 3 | 3 | 3 | 3 |
| Common blue violet | 0 | 2 | 0 | 2 | 0 | 2 | 3 | 3 |
| Crabgrass | 0 | 2 | 2 | 2 | 3 | 3 | 3 | 3 |
| Dandelion | 0 | 0 | 0 | 0 | 0 | 1 | 3 | 3 |
| Foxtail | 0 | 0 | 0 | 1 | 0 | 1 | 3 | 3 |
| Healall | 0 | 2 | 0 | 2 | 0 | 3 | 3 | 3 |
| Henbit | 0 | 0 | 0 | 1 | 0 | 2 | 3 | 3 |
| Goosegrass | 0 | 2 | 2 | 2 | 2 | 3 | 3 | 3 |
| Jap. honeysuckle | 0 | 2 | 0 | 2 | 0 | 3 | 3 | 3 |
| Nimblewill | 0 | 2 | 0 | 3 | 0 | 3 | 3 | 3 |
| Nutsedge, yellow | 0 | 0 | 0 | 0 | 0 | 1 | 3 | 3 |
| Oxalis | 0 | 3 | 0 | 3 | 3 | 3 | 3 | 3 |
| Purslane | 0 | 2 | 0 | 2 | 1 | 3 | 3 | 3 |
| Ragweed | 0 | 1 | 0 | 2 | 0 | 2 | 3 | 3 |
| White clover | 0 | 3 | 0 | 3 | 3 | 3 | 3 | 3 |

0 = no effect
1 = wilting and/or some change of color
2 = necrotic leaves
3 = complete collapse or dead After one day, most of the weeds sprayed with glyphosate plus dimethyl azelate were wilting or showed burned leaves while those weeds sprayed only with glyphosate were unaffected. After two days, the herbicidal effect of Sol. B was even more evident while only a few of the weeds treated with Sol. A were wilted or burned. After four days, most of the weeds sprayed with Sol. B were dead while some of the weeds sprayed with Sol. A were still unaffected. However, after fourteen days, all of the weeds on both plots were totally dead. Thus, the addition of dimethyl azelate to glyphosate substantially increases the herbicidal activity of the glyphosate without any detrimental effects.

EXAMPLE 2

Two solutions were prepared from 5.78% glufosinate (commercial "Finale"). In one, 1 fl. ounce of Finale was diluted to 32 fl. oz. (1 quart) with water. This was Sol. A. In the second, to 1 fl. oz. of Finale was added 10 gms. of tech. grade dimethyl azelate and the resultant mixture diluted to 32 fl. oz. This was Sol. B.

Sol. A and Sol. B were each sprayed from identical sprayers on grass and a variety of weeds including plantain, dandelion, speedwell, mustard and Japanese honeysuckle. In each case the leaves of the weeds were thoroughly wetted. The treated weeds were then observed for any changes over a period of 7 days with the results shown in the following table:

| Effect | After 1 day | | After 2 days | | After 4 days | | After 7 days | |
|---|---|---|---|---|---|---|---|---|
| Solution | A | B | A | B | A | B | A | B |
| Common chickweed | 0 | 1 | 0 | 3 | 1 | 3 | 3 | 3 |
| Jap. honeysuckle | 0 | 0 | 0 | 1 | 0 | 1 | 2 | 3 |
| Mustard | 0 | 1 | 0 | 2 | 1 | 3 | 2 | 3 |
| Speedwell | 0 | 1 | 0 | 1 | 1 | 1 | 3 | 3 |
| Plantain | 0 | 0 | 0 | 1 | 0 | 1 | 2 | 3 |

0 = no effect
1 = wilting and/or some change of color
2 = necrotic leaves
3 = complete collapse or dead After 1 day, honeysuckle and plantain were unaffected by both solutions. The chickweed and speedwell treated with Sol. A were unchanged. The Sol. B treated chickweed was wilted and had turned brown while the Sol. B treated speedwell had turned brown and had a dried out appearance. The mustard showed a discoloration and browning of the leaf tips.

After 2 days, all of the Sol. A treated weeds remained unaffected. Of the Sol. B treated weeds, the chickweed was totally dead and the speedwell appeared necrotic.

At 4 days, some of the Sol. A treated weeds had changed in appearance. All of the Sol. B treated plants showed visual effects with the chickweed and mustard totally dead. In a week, the Sol. A treated chickweed and speedwell were dead with the others showing leaf damage. All of the Sol. B treated weeds were dead.

EXAMPLE 3

Mugwort (Artemisia vulgaris L.) rhizomes 2 to 3 inches in length were collected from established plants and planted into soil-less media in 16 fl. oz. size containers. Each container was a replicate and contained one plant. On Day 0, 14 to 18 inch height single stem plants of mugwort were treated with the solutions shown in Table 1 with calibrated hand pump sprayers with constant agitation. Each plant was sprayed with 14 hand pumps for a nominal 40 gal/A spray volume application. Treatments were irrigated and fertilized as needed. The treated plants were observed for changes over 18 days with the results shown below.

| | | Concentration | % Necrosis | | % Control | | | |
|---|---|---|---|---|---|---|---|---|
| | TREATMENT | % W/W | Day 1 | Day 3 | Day 9 | Day 12 | Day 15 | Day 19 |
| 1. | Glyphosate[1] | 0.5 | 0 | 0 | 53 | 100 | 100 | 100 |
| 2 | Glyphosate + DMA[2] | 0.5 + 1.5 | 36 | 31 | 69 | 100 | 100 | 100 |
| 3 | DMA | 1.5 | 49 | 53 | 33 | 21 | 18 | 13 |
| 4. | Untreated Control | 0 | 0 | 0 | 0 | 0 | 0 | 0 |

[1]Glyphosate, isopropylamine salt, 62% water soluble concentrate, Cheminova Corp.
[2]Dimethyl azelate, 80% emulsifiable The data shows that 1.5% w/w dimethyl azelate (DMA) mixed with 0.5% w/w glyphosate significantly reduces the time required to control mugwort compared to glyphosate or dimethyl azelate applied alone.

EXAMPLE 4

Chlorimuron is a sulfonylurea-type postemergence herbicide, sold by duPont under the trade name "Classic".

Dimethyl azelate (80% technical grade with 20% emulsifier) was added with the dilute herbicidal spray solution to determine if the rapidity and effectiveness of weed control was improved. A single nozzle flat fan wand backpack sprayer with $CO_2$ propellant calibrated for 12 gal/A spray volume was used to apply the treatments with a handheld wand applicator and constant walking speed. Velvetleaf plants of 6 to 8 inch height with 3 plants per 16 fl oz container in soil-less media were treated with the mixtures shown in the table below. Each treatment was applied to 3 containers to provide 3 replications per treatment. The dilute spray solutions were agitated during application. The effects of the treatment were observed daily for 21 days with the following results:

| Herbicide | % W/W | lb.ai/A | % Necrosis After 1 Day | % Control 5 days | 9 days | 21 Days |
|---|---|---|---|---|---|---|
| 1. Chlorimuron | | 0.31 | 0 | 48 | 53 | 23 |
| 2. Chlorimuron + dimethyl azelate | 1.5 | 0.31 | 0 | 96 | 97 | 70 |
| 3. Dimethyl azelate | 1.5 | | 0 | 0 | 0 | 0 |
| 4. Untreated | 0 | 0 | 0 | 0 | 0 | 0 |

Dimethyl azelate increased the control of velvetleaf with chlorimuron compared to chlorimuron alone. Velvetleaf was tolerant to dimethyl azelate alone. Velvetleaf control appeared to decline at 21 days after application which indicated the chlorimuron treatment rate was too low to control the velvetleaf in the most effective manner. However, dimethyl azelate would provide the same enhancement to chlorimuron at increased application rate.

EXAMPLE 5

Morningglory, pitted (Ipomoea lacunosa L.) was seeded into soil-less media in 16 fl oz plastic pots with 3 plants established per pot. Each pot was a replication. When the morningglory plants had two true leaves, control treatments were applied by 2 manual hand pumps from a calibrated hand-pump sprayer. The spray application was a nominal 12 gpa spray volume. The Day 0 treatments were applied as 2 replications with constant agitation of the dilute spray solution. Treatments were evaluated for a 21 day interval after application as follows:

| TREATMENT | Concentration % W/W | % Epinasty[3] Day 5 | % Control Day 7 | Day 10 | Day 14 | Day 21 |
|---|---|---|---|---|---|---|
| 1. 2,4-D ester[1] | 0.3 | 90 | 60 | 75 | 88 | 100 |
| 2 2,4-D ester + DMA[2] | 0.3 + 2.0 | 95 | 85 | 93 | 94 | 100 |
| 3 DMA | 2.0 | 5 | 3 | 0 | 0 | 0 |
| 4. Untreated Control | 0 | 0 | 0 | 0 | 0 | 0 |

[1]2,4-D ester, low volatility formulation (4 lb.ai/gal)
[2]Dimethyl azelate, 80% emulsifiable
[3]Leaf distortion and downward twisting The addition of dimethyl azelate to 2,4-D reduces the time required for injury and control of morningglory.

EXAMPLE 6

Study 1:

Rye (Secale cereale L) was grown in 16 fl. oz. containers in soil less media until 4 inches in height and then treated with the herbicidal compositions shown in Table 1 by spraying the herbicidal compositions with 4 pumps of a calibrated hand pump sprayer. The spray volume delivered was 25 gal/Acre. The containers contained approximately 12 rye plants per pot and each container was one replication. Treatments were in full sun with no wind. The effects of the treatments were observed over 3 weeks with the following results recorded:

| Herbicide | % W/W | % Necrosis After 1 Day | After 3 Day | % Control 5 Days | 9 Days | 21 Days |
|---|---|---|---|---|---|---|
| 1. Sethoxydin | 0.01 | 0 | 3 | 24 | 79 | 94 |
| 2. Sethoxydin + dimethyl azelate | 0.01 + 3 | 5 | 16 | 71 | 88 | 95 |
| 3. Dimethyl azelate | 3 | 13 | 15 | 8 | 0 | 0 |
| 4. Untreated | 0 | 0 | 0 | 0 | 0 | 0 |

Sethoxydin, a cyclohexadione class herbicide, was obtained from BASF Corp. as "Poast". The dimethyl azelate was a technical grade obtained from Cognis Corp.

Study 2:

Another identical study was conducted with corn (Zea mays L.) with 3 plants per pot and 2 replications. The treatments were applied as 2 pumps per pot for a 13 gal/A spray volume to 6 inch height corn plants. The results were observed over the same time period as Study 1 with the collected data shown below:

| Herbicide | % W/W | % Necrosis After 1 Day | After 3 Day | % Control 5 Days | 9 Days | 21 Days |
|---|---|---|---|---|---|---|
| 1. Sethoxydin | 0.01 | 0 | 3 | 10 | 40 | 88 |
| 2. Sethoxydin + dimethyl azelate | 0.01 + 3 | 15 | 33 | 85 | 90 | 98 |
| 3. Dimethyl azelate | 3 | 18 | 15 | 13 | 0 | 0 |
| 4. Untreated | 0 | 0 | 0 | 0 | 0 | 0 |

The data shows that dimethyl azelate enhances the control of rye and corn with sethoxydin herbicide, a commercial graminicide for food crops and ornamental plants.

From the foregoing, it will be observed that numerous variations and modifications may be effected without departing from the true spirit and scope of the novel concepts of the invention.

What is claimed is:

1. A method for the prevention or elimination of undesired vegetation which comprises applying to the locus of the undesired vegetation a herbicidally effective amount of a composition comprising (i.) a post-emergent herbicide selected from the group of consisting of glyphosate, a phenoxy acid, glufosinate sulfonylurea and a cyclohexanedione; and (ii.) at least one carboxylic acid diester of the formula:

$$ROOC(CH_2)_nCOOR' \qquad (I)$$

wherein R and R' are independently selected from a $C_1$ to $C_4$ alkyl group and n is from about 5 to about 9.

2. The method of claim 1, wherein the amount of compound represented by the formula (I) in the composition is between from about 0.5 to about 5.0 percent by weight.

3. The method of claim 2, wherein the amount of compound represented by the formula (I) in the composition is between from about 1.5 to about 3.0 percent by weight.

4. The method of claim 1, wherein the at least one carboxylic acid diester is a diester of pimelic, suberic, azelaic, sebacic or undecanedioic acid.

5. The method of claim 4, wherein the at least one carboxylic acid diester is a methyl or ethyl diester of pimelic, suberic, azelaic, sebacic or undecanedioic acid.

6. The method of claim 5, wherein the at least one carboxylic acid diester is dimethyl azelate.

7. The method of claim 1, wherein the composition further comprises a diluent.

8. The method of claim 1, wherein the post-emergent herbicide is 2,4-D, chlorimuron or sethoxydim.

9. A herbicidal composition comprising (i.) a post-emergent herbicide selected from the group consisting of glyphosate, a phenoxy acid, glufosinate, sulfonylurea and a cyclohexanedione and (ii.) at least one carboxylic acid diester of the formula:

$$ROOC(CH_2)_nCOOR' \quad (I)$$

wherein R and R' are independently selected from a $C_1$ to $C_4$ alkyl group and n is from about 5 to about 9; and
further wherein the compound of formula (I) increases the herbicidal effect of the composition on the plant beyond that of a composition without the compound of formula (I).

10. The composition of claim 9, wherein the amount of the compound of formula (I) in the composition is between from about 0.5 to about 5.0 weight percent.

11. The composition of claim 10, wherein the amount of the compound of formula (I) in the composition is between from about 1.5 to about 3.0 percent by weight.

12. The composition of claim 9, wherein the at least one carboxylic acid diester is a diester of pimelic, suberic, azelaic, sebacic or undecanedioic acid.

13. The composition of claim 12, wherein the at least one carboxylic acid diester is a methyl or ethyl diester of pimelic, suberic, azelaic, sebacic or undecanedioic acid.

14. The composition of claim 13, wherein the at least one carboxylic acid diester is dimethyl azelate.

15. The composition of claim 9, wherein the composition further comprises a diluent.

16. The composition of claim 9, wherein the post-emergent herbicide is 2,4-D, chlorimuron or sethoxydim.

17. A method of controlling plant growth which comprises applying to a plant a herbicidally effective amount of a herbicidal composition comprising (i.) a post-emergent herbicide selected from the group consisting of phenoxy acid, benzoic acid, picolinic acid, glyphosate, glufosinate, sulfonylurea, imidazolinone, triezolopyrimidine sulfonanilide, pyrimidinyl oxydenzoate, aryloxyphenoxy propionate, cyclohexanedione and organic arsenical; and (ii.) at least one carboxylic acid diester of the formula:

$$ROOC(CH_2)_nCOOR' \quad (I)$$

wherein R and R' are independently selected from a $C_1$ to $C_4$ alkyl group and n is from about 5 to about 9; and
further wherein the amount of compound of formula (I) is sufficient to increase the herbicidal effect of the composition beyond that of the composition without the compound of formula (I).

18. The method of claim 17, wherein the amount of compound represented by the formula (I) in the composition is between from about 0,5 to about 5.0 percent by weight.

19. The method of claim 18, wherein the amount of compound represented by the formula (I) in the composition is between from about 1.5 to about 3.0 percent by weight.

20. The method of claim 17, wherein the at least one carboxylic acid diester is a diester of pimelic, suberic, azelaic, sebacic or undecanedioic acid.

21. The method of claim 20, wherein the at least one carboxylic acid diester is a methyl or ethyl diester of pimelic, suberic, azelaic, sebacic or undecanedioic acid.

22. The method of claim 21, wherein the at least one carboxylic acid diester is dimethyl azelate.

23. The method of claim 17, wherein the composition further comprises a diluent.

24. The method of claim 17, wherein the post-emergent herbicide is glyphosate, a phenoxy acid, glufosinate sulfonylurea, or cyclohexanedione.

25. The method of claim 24, wherein the post-emergent herbicide is 2,4-D, chlorimuron or sethoxydim.

\* \* \* \* \*